US00PP19371P2

(12) United States Plant Patent
Kaagman

(10) Patent No.: US PP19,371 P2
(45) Date of Patent: Oct. 21, 2008

(54) ***DAHLIA* PLANT NAMED 'GOALIA ROSSA'**

(50) Latin Name: *Dahlia variabilis*
Varietal Denomination: Goalia Rossa

(75) Inventor: Pim Kaagman, Andijk (NL)

(73) Assignee: Goldsmith Seeds Europe B.V., Andjik (NL)

( * ) Notice: Subject to any disclaimer, the term of this patent is extended or adjusted under 35 U.S.C. 154(b) by 0 days.

(21) Appl. No.: 11/894,579

(22) Filed: Aug. 21, 2007

(51) Int. Cl.
*A01H 5/00* (2006.01)

(52) U.S. Cl. ..... Plt./321
(58) Field of Classification Search ..... Plt./321
See application file for complete search history.

(56) References Cited

U.S. PATENT DOCUMENTS

PP16,085 P3 * 11/2005 Knudsen ..... Plt./321

OTHER PUBLICATIONS

UPOV ROM GTITM Database GTI Jouve Software May 2007, Citations for 'Goalia Rossa'.*

* cited by examiner

*Primary Examiner*—Wendy C. Haas
(74) *Attorney, Agent, or Firm*—Jondle & Associates, P.C.

(57) ABSTRACT

A new *Dhalia* plant particularly distinguished by its large, rose-colored flowers, good branching habit, and large, dark green leaves is disclosed.

2 Drawing Sheets

Genus and species: *Dahlia variabilis.*
Variety denomination: 'Goalia Rossa'.

BACKGROUND OF THE NEW PLANT

The present invention comprises a new and distinct cultivar of *Dhalia,* botanically known as *Dahlia variabilis,* and hereinafter referred to by the cultivar name 'Goalia Rossa'. The new cultivar originated from a hybridization made in June 1999 in Andijk, The Netherlands. The female parent was the bronze-yellow-flowered *Dhalia* proprietary line 'DT-79-1' (unpatented), and the male parent was the orange-flowered *Dhalia* proprietary line 'DU-43-1' (unpatented). The seeds produced by the hybridization were sown in February 2002 in Andijk, The Netherlands. A single plant selection was chosen for further evaluation and for asexual propagation in May 2002 in Andijk, The Netherlands.

The new cultivar was created in 1999 in Andijk, The Netherlands and has been asexually reproduced repeatedly by vegetative cuttings and tissue culture in Andijk, The Netherlands, and Gilroy, Calif. over a five-year period. The plant has also been trialed at Gilroy, Calif. Michigan, Andijk, The Netherlands and Hillscheid, Germany. The present invention has been found to retain its distinctive characteristics through successive asexual propagations.

Plant Breeder's Rights for this cultivar were applied for in the European Union on Jun. 19, 2006 and in Canada on Oct. 3, 2006. 'Goalia Rossa' has not been made publicly available more than one year prior to filing of this application.

SUMMARY OF THE INVENTION

The following are the most outstanding and distinguishing characteristics of this new cultivar when grown under normal horticultural practices in Gilroy, Calif.

1. Large, rose-colored flowers;
2. Good branching habit; and
3. Large, dark green leaves.

DESCRIPTION OF THE PHOTOGRAPHS

This new *Dahlia* plant is illustrated by the accompanying photographs which show overall plant habit including blooms, buds, and foliage of the plant; the photographs are of 20-to 24-week old plants grown in a greenhouse in Hillscheid, Germany in 2006; the colors shown are as true as can be reasonably obtained by conventional photographic procedures.

DESCRIPTION OF THE NEW CULTIVAR

Figure 1:
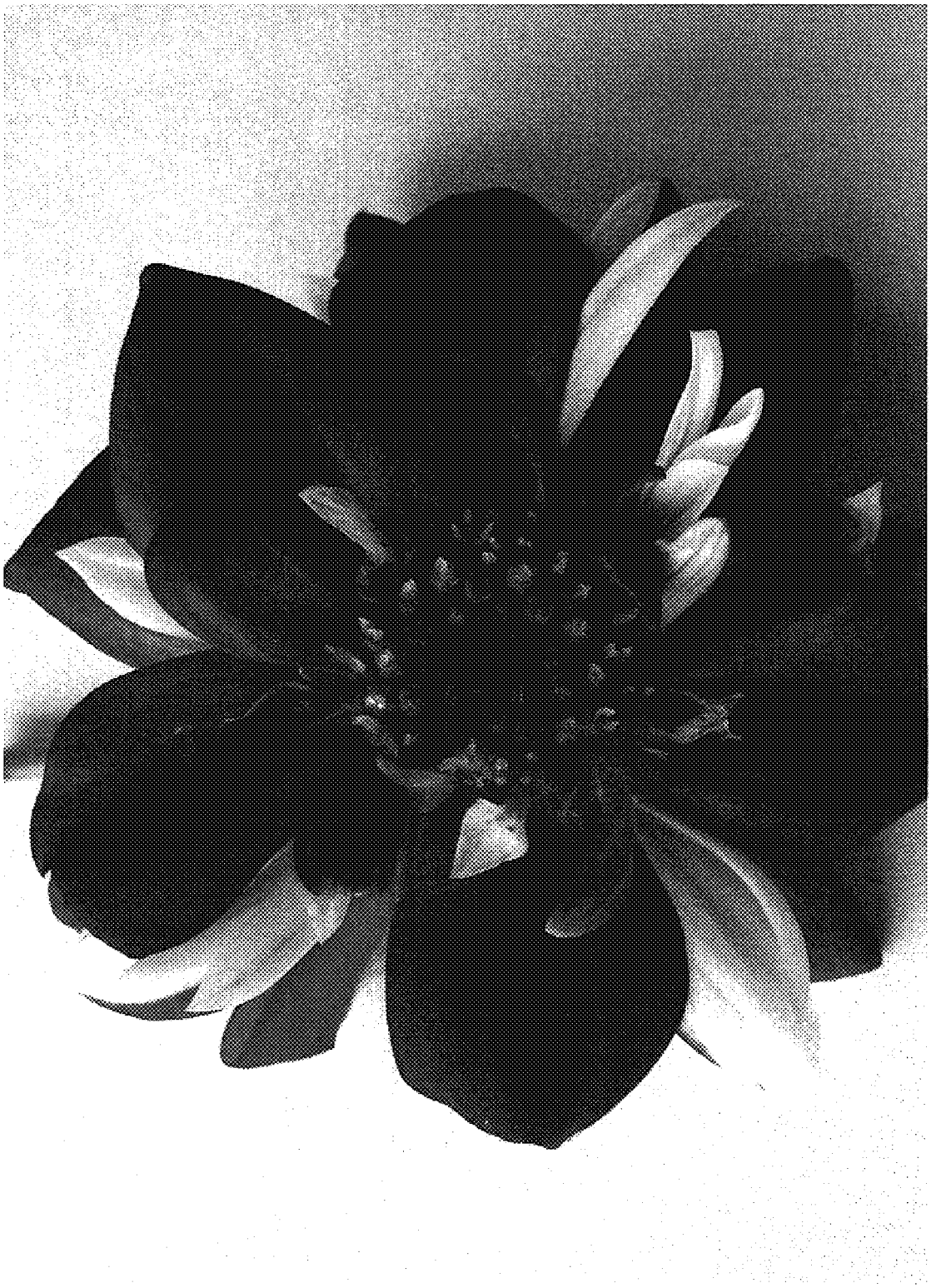
FIG. 1 shows a close-up of the mature flowers.
Figure 2:
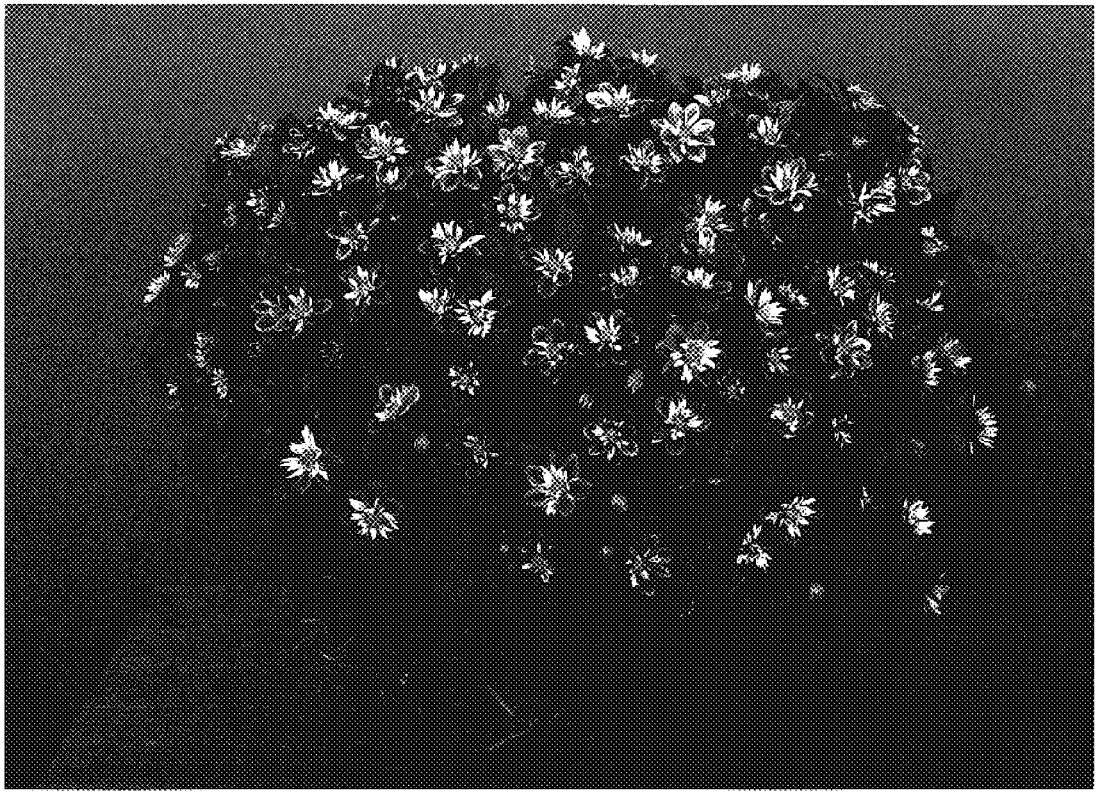
FIG. 2 shows the overall plant habit, including blooms, buds, and foliage.

The following detailed descriptions set forth the distinctive characteristics of 'Goalia Rossa'. The data which define these characteristics were collected from asexual reproductions carried out in Ontario, Canada. The plant history was taken on 16-week-old plants grown in 6-inch azalea pots in the spring and summer seasons in a greenhouse. Two terminal pinches were made at a young plant stage. No plant growth regulators were used. The plants were grown under a poly covered hoop and then moved indoors. Color readings were taken outdoors in the summer season under natural light. Color references are primarily in the R.H.S. Colour Chart of The Royal Horticultural Society of London (R.H.S.) (2001 edition).

DESCRIPTION OF THE NEW PLANT

Classification:
*Family.*—Asteraceae.
*Botanical name.*—*Dahlia variabilis.*

Parentage:
*Female parent.*—'DT-79-1' bronze-yellow-flowered *Dahlia* proprietary line (unpatented).
*Male parent.*—'DU-43-1' orange-flowered *Dhalia* proprietary line (unpatented).
Growth:
*Form.*—Upright.
*Habit.*—Compact and mounding.
*Growth and branching habit.*—Good, vigorous habit; excellent branching.
*Height* (*from top of soil*).—20.0 cm to 22.0 cm.
*Width.*—35.0 cm to 40.0 cm.
*Time to produce a finished flowering plant.*—7 to 9 weeks for a 4-to 6-inch pot.
*Outdoor plant performance.*—Free flowering, used in patio planters, mixed-container plantings, or in garden beds.
*Time to initiate and develop roots.*—22 to 28 days.
*Root description.*—Fibrous and white.
Leaves:
*Arrangement.*—Opposite, single, simple; sometimes lobed.
*Shape.*—Elliptical.
*Apex.*—Acute.
*Base.*—Attenuate.
*Margin.*—Deeply and widely serrate.
*Length* (*fully expanded*).—7.1 cm to 7.4 cm.
*Width* (*fully expanded*).—3.4 cm to 3.7 cm.
*Texture.*—Leathery, smooth.
*Color.*—Immature: Upper surface: RHS 137B. Lower surface: RHS 148D with a silvery sheen. Mature: Upper surface: RHS 137A. Lower surface: RHS 148D with a silvery sheen.
*Venation.*—Arrangement: Pinnate. Color: RHS 143C.
*Petiole.*—Color: RHS 143C along the sides, almost transparent in the middle. Length: 2.1 cm to 2.4 cm. Width: 0.3 cm. Texture: Smooth, glabrous.
Stems:
*Number of branches per plant.*—4 to 6.
*Length.*—18.0 cm to 22.0 cm.
*Diameter.*—0.3 cm to 0.4 cm.
*Internode length.*—3.1 cm to 3.4 cm.
*Color.*—RHS 146B, with some RHS 143C blotches mixed in.
*Texture.*—Smooth, glabrous.
*Anthocyanin.*—Absent.
*Penduncle.*—Color: Lighter than RHS 143C. Length: 6.0 cm to 6.2 cm. Diameter: 0.2 cm. Texture: Smooth, glabrous.
Bud:
*Shape.*—Orbicular when immature, to ovate when mature.
*Diameter.*—0.8 cm to 1.0 cm.
*Length.*—0.8 cm to 1.1 cm.
*Color* (*just before ray florets unfold*).—RHS 59A.
Inflorescence:
*Type.*—Composite; borne on terminals above foliage; semi-double flowers, florets face upward or outward.
*Blooming habit.*—Continuous throughout the growing season; excellent floriferousness.
*Quantity of inflorescences per plant.*—15 to 20.
*Lastingness of individual blooms on the plant.*—7 to 12 days.
*Fragrance.*—None.
*Inflorescence diameter* (*mature*).—5.2 cm to 7.0 cm.
Disc floret:
*Quantity* (*per inflorescence*).—30 to 40.
*Shape.*—Elongated, cylindrical, shiny.
*Color.*—RHS 2A.
*Length.*—1.0 cm to 1.1 cm.
*Diameter.*—0.2 cm to 0.3 cm.
*Apex.*—5-pointed, each acute.
*Ray floret.*—Quantity: 8 to 15, in several whorls. Length: 2.2 cm to 2.5 cm. Width: 1.6 cm to 1.9 cm. Color: Immature: Upper surface: RHS 59A. Lower surface: RHS 72A with RHS 155B streaks; RHS 145C veins. Mature (both surfaces): Velvety RHS 60A; with RHS 59A overlay; maturing to RHS 60B, many with RHS N74B irregular blotches mainly at the margins or the apex. Apex: Praemorse. Base: Fused. Margin: Entire. Texture: Papillose.
*Petaloids.*—Quantity: 3 to 5 per ray floret. Color (both surfaces): Many are RHS 157D, but whiter, some with a hint of RHS N78B at the margins, while the lower surface is about the same coloring; others are about RHS 60C, while the lower surface is close to RHS N155C with RHS 60D streaks. Length: 1.0 cm to 2.1 cm. Diameter: 0.5 cm. Shape: Narrow elliptic. Apex: Acute. Margin: Entire. Base: Attenuate. Texture: Papillose.
*Involucral bracts.*—Quantity (per inflorescence): 5. Shape: Elliptical, almost spatulate. Length: 0.9 cm to 1.0 cm. Width: 0.5 cm. Color (both surfaces): RHS 137B. Apex: Acute. Base: Attenuate. Margin: Entire. Texture: Smooth, glabrous.
Reproductive Organs:
*Androecium.*—Location: Present on disc florets only. Quantity per floret: 1. Anther. Color: RHS 21A with RHS N34A infused. Length: 0.4 cm. Filament length: 0.8 cm. Filament color: RHS N155C. Pollen color: RHS 17A. Pollen amount: Moderate.
*Gynoecium.*—Location: Present on ray and disc florets. Quantity per floret: 1. Pistil length: Ray florets: 0.9 cm. Disc florets: 1.0 cm. Stigma: Color: RHS 3B. Style: Color: RHS 154C.
Fruit and seed set: Has not been observed.
Disease and insect resistance: Has not observed.

COMPARISON WITH PARENTAL AND COMMERCIAL CULTIVARS

'Goalia Rossa' differs from the female parent, 'DT-79-1' (unpatented) in that 'Goalia Rossa' has larger, rose-colored flowers while 'DT-79-1' has smaller, bronze and yellow-colored flowers. Additionally, 'Goalia Rossa' has a better branching habit than 'DT-79-1'.

'Goalia Rossa' differs from the male parent, 'DU-43-1' (unpatented) in that 'Goalia Rossa' has rose-colored flowers, while 'DU-43-1' has orange-colored flowers. Additionally, 'Goalia Rossa' has larger, darker leaves than 'DU-43-1'.

'Goalia Rossa' differs from the commercial cultivar 'Bahamas' (U.S. Plant patent application No. 16,085) (European Union Plant Variety Propection Application No. EU15615) in that 'Goalia Rossa' is a collerette type, rose-purplish flower, while 'Bahamas' is a more decorative, reddish-purple flower. Additionally, 'Goalia Rossa' has smaller and lighter green foliage with stronger serrations than 'Bahamas'.

I claim:

1. A new and distinct cultivar of *Dahlia* plant as shown and described herein.

* * * * *